United States Patent
Burns et al.

(10) Patent No.: US 6,458,935 B1
(45) Date of Patent: Oct. 1, 2002

(54) RADIOLABELED FARNESYL-PROTEIN TRANSFERASE INHIBITORS

(75) Inventors: H. Donald Burns, Harleysville; Terence G. Hamill, Lansdale; Raymond E. Gibson, Holland, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/668,637

(22) Filed: Jun. 12, 2000

Related U.S. Application Data

(60) Provisional application No. 60/140,536, filed on Jun. 23, 1999.

(51) Int. Cl.[7] ............... C07D 403/04; C07C 255/50
(52) U.S. Cl. ................... 534/10; 544/370; 558/414
(58) Field of Search .................. 534/10; 544/224, 544/358, 366, 386, 392, 406, 336, 370; 548/311.1, 335.8, 343.5; 558/414

(56) References Cited

U.S. PATENT DOCUMENTS

| | | |
|---|---|---|
| 4,960,815 A | 10/1990 | Moos |
| 4,994,258 A | 2/1991 | Burns et al. |
| 5,141,851 A | 8/1992 | Brown et al. |
| 5,238,922 A | 8/1993 | Graham et al. |
| 5,340,828 A | 8/1994 | Graham et al. |
| 5,352,705 A | 10/1994 | Deana et al. |
| 5,439,918 A | 8/1995 | deSolms et al. |
| 5,504,212 A | 4/1996 | deSolms et al. |
| 5,534,537 A | 7/1996 | Ciccarone et al. |
| 5,571,835 A | 11/1996 | Anthony et al. |
| 5,578,629 A | 11/1996 | Ciccarone et al. |
| 5,609,849 A | 3/1997 | Kung |
| 5,856,326 A * | 1/1999 | Anthony et al. ............ 514/252 |
| 5,859,015 A * | 1/1999 | Graham et al. ............ 514/255 |
| 6,060,038 A * | 5/2000 | Burns et al. ............... 424/1.81 |

FOREIGN PATENT DOCUMENTS

| | | | |
|---|---|---|---|
| WO | WO 95/25086 | 9/1995 | |
| WO | WO 96/00736 | 1/1996 | |
| WO | WO 96/30343 | 10/1996 | |
| WO | 99-00654 | * | 1/1999 |

OTHER PUBLICATIONS

J. Labelled Cpd. Radiopharm., vol. 42, Suppl. 1 (1999), pp. S204–S206, by W–S Eng, et al.
J. of Biol. Chem., vol. 268, No. 11, pp. 7617–7620 (1993), by Gibbs, et al.
J. of Biol. Chem., vol. 266, No. 24, pp. 15575–15578 (1991), by Goldstein, et al.
Exp. Opin. Ther. Patents, vol. 5, No. 12, pp. 1269–1285 (1995), by Graham.
J. of Biol. Chem., vol. 270, No. 11, pp. 6221–6226 (1995), by James, et al.
Nature Medicine, vol. 1, No. 8, pp. 792–797 (1995), by Kohl, et al.
Proc. Natl. Acad. Sci. USA, Med. Sciences, vol. 91, pp. 9141–9145 (1994), by Kohl, et al.
Biochemistry, vol. 31, pp. 3800–3807 (1992), by Pompliano.
Cancer Research, vol. 55, pp. 5302–5309 (1995), by Sepp–Lorenzino, et al.
Exp. Opin. Ther. Patents, vol. 6, No. 12, pp. 1295–1304 (1996), by Graham, et al.
Science, vol. 260, pp. 1934–1937 (1993), by Kohl, et al.
J. of Labelled Compounds & Radiopharm., vol. 42, S30–32 (1999), by T. G. Hamill, et al.
J. of Nuclear Med., vol. 40, No. 5, Suppl. 99P (1999), No. 400 by R. E. Gibson, et al.

* cited by examiner

*Primary Examiner*—T. A. Solola
(74) *Attorney, Agent, or Firm*—Dianne Brown; Mark R. Daniel

(57) ABSTRACT

The present invention is directed toward radiolabeled farnesyl-protein transferase inhibitor compounds which are useful to label FPTase in assays, whether cell-based, tissue-based or in whole animal. The tracers can also be used in competitive binding assays to obtain information on the interaction of unlabeled FTIs with FPTase.

7 Claims, No Drawings

RADIOLABELED FARNESYL-PROTEIN TRANSFERASE INHIBITORS

DOMESTIC PRIORITY CLAIM

The priority of U.S. Provisional Application No. 60/140,536 filed on Jun. 23, 1999, is claimed under 35 U.S.C. §119(e).

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation which is capable of detecting radiation emitted from radiotracers administered to such living subjects. The information obtained can be reconstructed to provide planar and tomographic images which reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radio-tracers are available for obtaining useful information concerning such things as cardiac function, myocardial blood flow, lung perfusion, liver function, brain blood flow, regional brain glucose and oxygen metabolism.

Compounds can be labeled with either positron or gamma emitting radionuclides. For imaging, the most commonly used positron emitting radionuclides are $^{11}$C, $^{18}$F, $^{15}$O and $^{13}$N, all of which are accelerator produced, and have half lives of 20, 110, 2 and 10 min. respectively. Since the half-lives of these radionuclides are so short, it is only feasible to use them at institutions which have an accelerator on site for their production, thus limiting their use. Several gamma emitting radiotracers are available which can be used by essentially any hospital in the U.S. and in most hospitals worldwide. The most widely used of these are $^{99m}$Tc, $^{201}$Tl, and $^{123}$I. $^{123}$I is particularly useful as a radiotracer for imaging applications because of its ability to form covalent bonds with carbon which, in many cases, are stable in vivo and which have well-understood effects on physiochemical properties of small molecules.

In the past decade, one of the most active areas of nuclear medicine research has been the development of receptor imaging radio-tracers. These tracers bind with high affinity and specificity to selective hormone receptors and neuroreceptors. Successful examples include radiotracers for imaging the following receptor systems: estrogen, muscarinic, dopamine D1 and D2, and opiate.

Currently available chemotherapeutic drugs for treating neoplastic diseases act by disrupting fundamental mechanisms concerned with cell growth, mitotic activity, differentiation and function. The capacity of these drugs to interfere with normal mitosis and cell division in rapidly proliferating tissues is the basis for their therapeutic application as well as toxic properties. As a result, clinical doses of anti-tumor drugs are a compromise between efficacy and toxicity such that therapeutic doses are usually set close to the toxic levels in order to maximize efficacy. In a similar manner, dose selection for clinical evaluation of new anti-tumor drugs is a function of the toxicity of the drug where doses used in Phase II and III trials are often the maximally tolerated doses.

The Ras proteins (Ha-Ras, Ki4a-Ras, Ki4b-Ras and N-Ras) are part of a signaling pathway that links cell surface growth factor receptors to nuclear signals initiating cellular proliferation. Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

At least 3 post-translational modifications are involved with Ras membrane localization, required for normal and oncogenic function, and all 3 modifications occur at the C-terminus of Ras. The Ras C-terminus contains a sequence motif termed a "CAAX" or "Cys -Aaa$^1$-Aaa$^2$-Xaa" box, which, depending on the specific sequence, serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. Recently, it has been shown that an inhibitor of farnesyl-protein transferase blocks the growth of ras-dependent tumors in nude mice (N. E. Kohl et al., *Proc. Natl. Acad. Sci. U.S.A.*, 91:9141–9145 (1994) and induces regression of mammary and salivary carcinomas in ras transgenic mice (N. E. Kohl et al., *Nature Medicine*, 1:792–797 (1995).

Farnesyl transferase inhibitors (FTIs) represent a new pharmacological approach to the treatment of cancer that is mechanism-based and does not rely on a cytotoxic mechanism of action. Ideally, therapeutically effective doses of FTIs will not be limited by cytotoxic side effects and these compounds will have a much larger therapeutic window than currently available anti-tumor drugs.

Farnesyl-protein transferase inhibitors may also be useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the instant composition to a mammal in need of such treatment. For example, a component of NF-1 is a benign proliferative disorder.

Use of farnesyl-protein transferase inhibitors in the prevention of restenosis after percutaneous transluminal coronary angioplasty by inhibiting neointimal formation has recently been described (C. Indolfi et al. *Nature medicine*, 1:541–545(1995)). It has been disclosed that farnesyl-protein transferase inhibitors may also be useful in the treatment and prevention of polycystic kidney disease (D. L.

Schaffner et al. *American Journal of Pathology*, 142:1051–1060 (1993) and B. Cowley, Jr. et al. *FASEB Journal*, 2:A3160 (1988)).

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

In contrast to cytotoxic chemotherapeutic agents, a more rational approach for estimating clinically-effective doses can be used with FTIs, i.e. it may not be necessary to titrate doses in a patient until toxic effects are observed if that dose is considerably higher than needed to provide the desired effect on tumor growth. Alternatively, if dose-limiting toxicity is observed with the clinical FTI, the dose may not be sufficient to inhibit the enzyme to the extent needed to block tumor growth. Demonstration of clinical efficacy using inhibition of tumor growth or regression in tumor size as an endpoint will require considerable time (weeks to months) and, therefore, dose selection for these trials is very important. Plasma drug concentrations are often used for clinical dose selection, however this endpoint may be a poor surrogate for the drug concentration at the pharmacological target, especially when the site of action is intracellular, such as is the case with farnesyl transferase. PET (Positron Emission Tomography) radiotracers and imaging technology may provide a powerful method for clinical evaluation and dose selection of FTIs. Using a carbon-11 or fluorine-18 labeled radiotracer that enters cells and provides a farnesyl transferase (FPTase) enzyme-specific image in tumors and other tissues, the dose required to saturate FPTase can be determined by the blockade of the PET radiotracer image in humans. The rationale for this approach is as follows: anti-tumor efficacy of FTIs is a consequence of the extent of enzyme inhibition, which in turn is a function of the degree of drug-enzyme occupancy.

Radiolabeled farnesyl-protein transferase inhibitor compounds have recently been described in WO 99/00654, which published on Jan. 7, 1999.

It is, therefore, an object of this invention to develop radiolabeled farnesyl-protein transferase inhibitor compounds that would be useful not only in traditional imaging applications, but would also be useful in assays, both in vitro and in vivo, for labeling the enzyme and for competing with unlabeled farnesyl-protein transferase inhibitors (FTIs). It is a further object of this invention to develop novel assays which comprise such radiolabeled compounds.

It is also the object of this invention to provide for a radiolabeled farnesyl-protein transferase inhibitor compound which is optimized for in vivo imaging and is therefore useful for determining the appropriate clinical doses of an FTI which will be used to assess anti-tumor efficacy in humans.

SUMMARY OF THE INVENTION

The present invention is directed toward radiolabeled farnesyl-protein transferase inhibitor compounds, as illustrated by formula I below

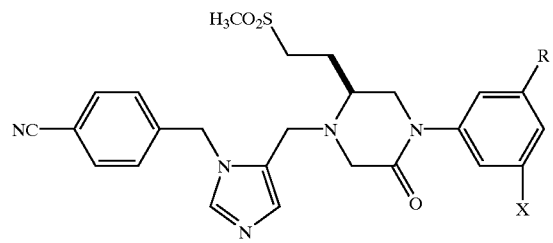

wherein
R is $O(CH_2)_n$halo;
X is a radionuclide comprising $^3H$, $^{11}C$, $^{18}F$, $^{125}I$, $^{82}Br$, $^{123}I$, $^{124}I$, $^{131}I$, $^{75}Br$, $^{76}Br$, $^{15}O$, $^{13}N$, $^{211}At$, or $^{77}Br$; and
n is 1 to 6;
or a pharmaceutically acceptable salt thereof, which are useful to label FPTase in assays, whether cell-based, tissue-based or whole animal. The tracers can also be used in competitive binding assays to obtain information on the interaction of unlabeled FTIs with FPTase.

DETAILED DESCRIPTION OF THE INVENTION

The present invention is directed toward radiolabeled farnesyl-protein transferase inhibitor compounds of formula I

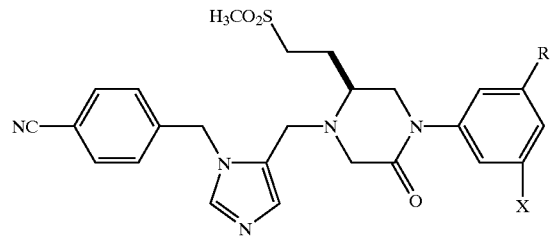

wherein
R is $O(CH_2)_n$halo;
X is a radionuclide comprising $^3H$, $^{11}C$, $^{18}F$, $^{125}I$, $^{82}Br$, $^{123}I$, $^{124}I$, $^{131}I$, $^{75}Br$, $^{76}Br$, $^{15}O$, $^{13}N$, $^{211}At$, or $^{77}Br$; and
n is 1 to 6;
or a pharmaceutically acceptable salt thereof
In a second embodiment of the instant invention, the radiolabeled farnesyl-protein transferase inhibitor compounds are illustrated by formula I

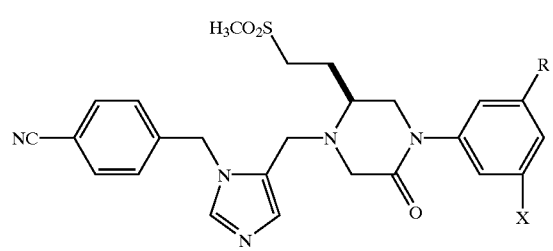

wherein
R is $O(CH_2)_n{}^{18}F$;

X is $^{127}$I; and n is 1 to 6;

or a pharmaceutically acceptable salt thereof.

In a third embodiment of the invention, the radiolabeled farnesyl-protein transferase inhibitor compounds are illustrated by formula II

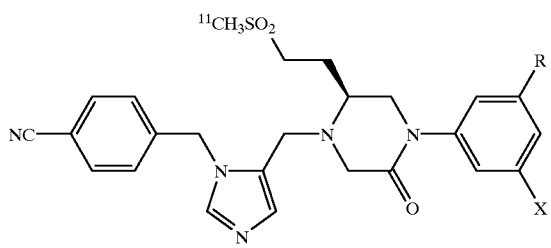

II wherein

R is O(CH$_2$)$_n$halo

X is $^{127}$I; and n is 1 to 6;

or a pharmaceutically acceptable salt thereof.

Examples of radiolabeled farnesyl protein transferase inhibiting compounds include the following:

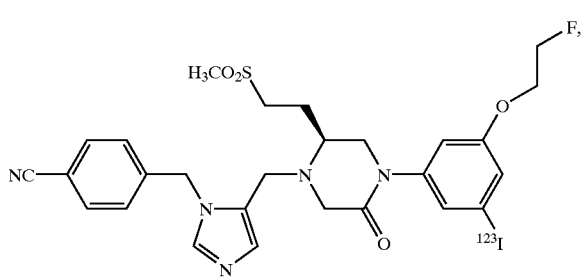

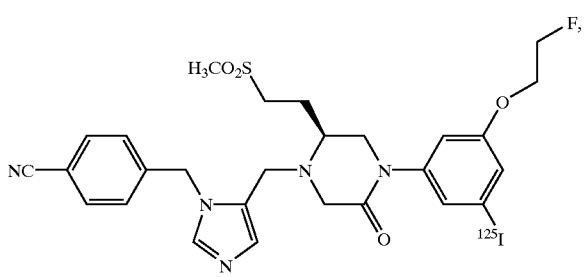

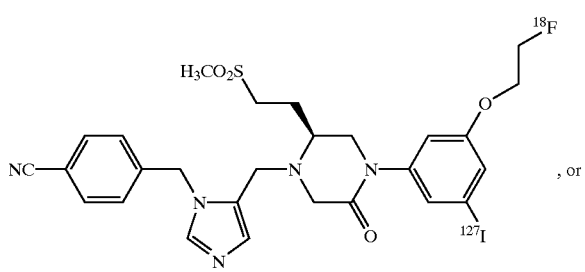

, or

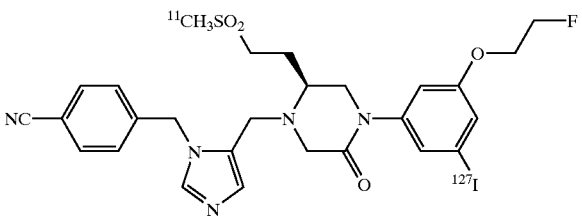

or a pharmaceutically acceptable salt thereof.

The compounds of the instant invention are useful for labeling farnesyl-protein transferase (FPTase) in assays, whether cell-based, tissue-based or in whole animal. Such radiolabeled compounds can also be used in competitive binding assays to obtain information on the interaction of unlabeled FTIs with FPTase. The in vitro and in vivo assays utilizing the instant radiolabeled compounds are useful in identification of novel compounds that are highly selective inhibitors of FPTase and are therefore useful in the treatment of cancer. The radiolabeled compounds may also be useful in autoradiography and as diagnostic imaging agents.

"Halogen" or "halo" as used herein means fluoro, chloro, bromo and iodo.

As noted above in the first embodiment of the instant invention, suitable radionuclides, designated as substituent "X", that may be incorporated in the instant compounds include $^3$H (also written as T), $^{11}$C, $^{18}$F, $^{125}$I, $^{82}$Br, $^{123}$I, $^{124}$I, $^{131}$I, $^{75}$Br, $^{76}$Br, $^{15}$O, $^{13}$N, $^{211}$At, and $^{77}$Br. The radionuclide that is incorporated in the instant radiolabeled compounds will depend on the specific analytical or pharmaceutical application of that radiolabeled compound. Thus, for in vitro FPTase labeling and competition assays, inhibitor compounds that incorporate $^3$H, $^{125}$I or $^{82}$Br will generally be most useful. For diagnostic imaging agents, inhibitor compounds that incorporate a radionuclide selected from 11C, $^{18}$F, $^{123}$I, $^{125}$I, $^{124}$I, $^{131}$I, $^{75}$Br, $^{76}$Br or $^{77}$Br are preferred. In certain applications incorporation of a chelating radionuclide such as Tc$^{99m}$ may also be useful. Preferably, in the first embodiment of the instant invention, X comprises $^{125}$I, $^{123}$I, $^{124}$I, $^{82}$Br, $^{75}$Br, $^{76}$Br, SnMe$_3$ and $^{77}$Br. Most preferably, in the first embodiment of the instant invention, X comprises $^{125}$I or 123I.

In the second and third embodiments of the instant invention, X is designated as $^{127}$I since the compounds are radiolabeled with a suitable radionuclide (such as $^{11}$C or $^{18}$F) at another position.

The labeled farnesyl-protein transferase inhibitor should bind with a high affinity to FPTase. Preferably, the labeled inhibitor has an IC$_{50}$≦10 nM, and most preferably the labeled inhibitor has an IC$_{50}$≦5nM.

Because the FPTase that is interacting with the labeled inhibitor is generally cellular FPTase, the labeled inhibitor of the instant invention must be diffusable across the cell membrane and remain diffusable after binding to FPTase to avoid intracellular accumulation of labeled inhibitor which might contribute to greater assay background noise. Therefore, it is preferred that the labeled inhibitor have a lipo-philicity (partition coefficient) in the range of about 0.5 to about 3.5 and preferably in the range of about 1.0 to about 3.0. It is also preferred that the labeled inhibitor chosen is generally free from nonspecific intracellular interactions that would alter the compounds permeability or effect its FPTase binding affinity. Therefore, while many farnesyl-protein transferase inhibitors have been described that incorporate a thiol moiety, the nonspecific interactions associated with such a moiety disfavor those inhibitors. Similarly, ester prodrugs which exhibit potent intercellular FPTase inhibitory activity only upon conversion to their corresponding acid within the cell are also disfavored because the conversion to the active acid would alter the permeability of the labeled inhibitor.

Radiolabeled FPTase inhibitor compounds, when labeled with the appropriate radionuclide, are potentially useful for diagnostic imaging, basic research, and radiotherapeutic applications. Specific examples of possible diagnostic imaging applications include:

1. Location of primary and metastatic tumors of the pancreas; exocrine tumors;
2. Diagnosis and staging of colorectal carcinoma;
3. Diagnosis and staging of myeloid leukemia;
4. Diagnosis and staging of neurological tumors;
5. Diagnosis and staging of the benign proliferative disorder associated with NF-1;
6. Diagnosis of neointimal formation resulting from percutaneous transluminal coronary angioplasty; and
7. Diagnosis and staging of polycystic kidney disease.

Specific examples of possible radiotherapeutic applications include:

1. Radioimmunoassay of FPTase inhibitors;
2. Radioimmunoassay to determine the concentration of FPTase in a tissue sample; and
3. Autoradiography to determine the distribution of FPTase in a mammal or an organ or tissue sample thereof.

For the use of the instant compounds as diagnostic imaging agents the radiolabeled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous.

For intramuscular, intraperitoneal, subcutaneous and intravenous use, sterile solutions of the labeled compound are usually prepared, and the pH of the solutions should be suitably adjusted and buffered. For intravenous use, the total concentration of solutes should be controlled in order to render the preparation isotonic. For oral use of a diagnostic imaging combination according to this invention, the selected combination or compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredients are combined with emulsifying and suspending agents. If desired, certain sweetening and/or flavoring agents may be added.

Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

As used herein, the term "composition" is intended to encompass a product comprising the specified ingredients in the specific amounts, as well as any product which results, directly or indirectly, from combination of the specific ingredients in the specified amounts.

When a radiolabeled compound according to this invention is administered into a human subject, the amount required for diagnostic imaging will normally be determined by the prescribing physician with the dosage generally varying according to the age, weight, and response of the individual patient, as well as the quantity of emission from the radionuclide. However, in most instances, an effective amount will be the amount of compound sufficient to produce emissions in the range of from about 1–5 mCi.

In one exemplary application, administration occurs in an amount of radiolabeled compound of between about 0.005 µg/kg of body weight to about 50 µg/kg of body weight per day, preferably of between 0.02 µg/kg of body weight to about 3 µg/kg of body weight. A particular analytical dosage that comprises the instant composition includes from about 0.5 µg to about 100 µg of a labeled farnesyl-protein transferase inhibitor. Preferably, the dosage comprises from about 1 µg to about 50 µg of a radiolabeled farnesyl-protein transferase inhibitor.

The following illustrative procedure may be utilized when performing PET imaging studies on patients in the clinic.

The patient is fasted for at least 12 hours allowing water intake ad libitum, and is premedicated with 0.3–0.4 mL Acepromazine injected i.m. on the day of the experiment. A 20 G two inch venous catheter is inserted into the contralateral ulnar vein for radiotracer administration.

The patient is positioned in the PET camera and a tracer dose of $[^{15}O]H_2O$ administered via i.v. catheter. The image thus obtained is used to insure that the patient is positioned correctly to include liver, kidneys, tumors and pancreas. Subsequently, a $[^{11}C]$ radiolabeled farnesyl-protein transferase inhibitor (<20 mCi) is administered via i.v. catheter. Following the acquisition of the total radiotracer image, an infusion is begun of the farnesyl-protein transferase inhibitor which is being clinically evaluated (clinical candidate) at one of three dose rates (0.1, 1 or 10 mpk/day). After infusion for 2.5 hrs, the $[^{11}C]$ radiolabeled farnesyl-protein transferase inhibitor is again injected via the catheter. Images are again acquired for up to 90 min. Within ten minutes of the injection of radiotracer and at the end of the imaging session, 1 ml blood samples are obtained for determining the plasma concentration of the clinical candidate.

For uninhibited distribution of radiotracer, regions of interest (ROIs) are drawn on the reconstructed image includes the tumor, kidney cortex and a region of liver which is removed from the gallbladder images. These regions are used to generate time activity curves obtained in the absence of inhibitor or in the presence of the clinical candidate at the various infusion doses examined. Data are expressed as radioactivity per unit time per unit volume (µCi/cc/mCi injected dose). Inhibition curves are generated from the data obtained in a region of interest obtained starting at 70 min. post-injection of radiotracer. At this time, clearance of non-specific binding has reached steady state. The $ID_{50}$ values were obtained by curve fitting the dose-rate/inhibition curves with equation iii:

$$B = \frac{A_0 - (A_0 \times I)}{(ID_{50} + I) + NS} \tag{iii}$$

where B is the %-Dose/g of radiotracer in tissues for each dose of clinical candidate, $A_0$ is the specifically bound radiotracer in a tissue in the absence of clinical candidate, I is the injected dose of inhibitor, $ID_{50}$ is the dose of clinical candidate which inhibits 50% of specific radiotracer binding to FPTase, and NS is the amount of non-specifically bond radiotracer.

In the present method, amino acids which are disclosed are identified both by conventional 3 letter and single letter abbreviations as indicated below:

| Alanine | Ala | A |
| --- | --- | --- |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds used in the present method may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., R, n, etc.) at a particular location in a molecule be independent of its definitions elsewhere in that molecule. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

Abbreviations used in the description of the chemistry and in the Examples that follow are:

| Ac$_2$O | Acetic anhydride; |
| --- | --- |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| Et$_3$N | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| Me | methyl or methylene; |
| MeOH | methanol; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran; |
| MMPP | Magnesium monoperoxyphthalate hexahydrate; or Monoperoxyphthalic acid, magnesium salt. |

The compounds are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Pharmaceutically acceptable salts include conventional non-toxic salts or quarternary ammonium salts formed, e.g., from non-toxic inorganic or organic acids. Non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluene-sulfonic, methanesulfonic, ethane disulfonic, oxalic, isethionic, trifluoroacetic, and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The instant invention is also directed to an assay that measures the competition between a farnesyl transferase inhibitor test compound and a radiolabeled farnesyl transferase inhibitor for binding to farnesyl transferase binding sites in living cells. Such an assay for example would comprise the steps of:

a) culturing monolayers of the cells;
b) exposing a monolayer of cells to growth media containing the radiolabeled farnesyl transferase inhibitor in the presence or absence of the test compound;
c) washing the cells;
d) counting the radiation emitted by the cells; and
e) comparing the radiation emitted by cells exposed to the radiolabeled farnesyl transferase inhibitor and the test compound to the radiation emitted by cells exposed to only the radiolabeled farnesyl transferase inhibitor.

In an embodiment of the above described assay, the monolayer of cells first exposed to growth media containing only the radiolabeled FTI and then, after this pre-exposure, the cells are exposed to growth media containing the test compound. The period of pre-exposure is preferably from about 5 min. to about 1 hour.

Farnesyl-protein transferase inhibitor compounds which incorporate a radionuclide may be prepared by first synthesizing an unlabeled inhibitor that optionally incorporates an iodo or bromo moiety and then exchanging a hydrogen or halogen moiety with an appropriate radionuclide using techniques well known in the art. Syntheses of unlabeled FPTase inhibitors have been generally described in the patent publications cited hereinabove. Syntheses of particular FPTase inhibitors is described below.

These reactions may be employed in a linear sequence to provide the compounds of the invention or they may be used to synthesize fragments which are subsequently joined by the alkylation reactions described in the Schemes.

Synopsis of Schemes 1–4

In Schemes 1–3, variable "n" is selected from 1 to 6.

Schemes 1 and 2 shows the synthetic route used to synthesize the iodine-123 and iodine-125 labelled farnesyl transferase inhibitors. As shown in Scheme 1, commercially available 2-methoxy-4-nitroaniline is brominated using NBS/acetonitrile and is then deaminated. The resulting aryl methyl ether (2) is demethylated to give the corresponding phenol (3). Alkylation of the phenol (3) using the appropriate haloalkyl bromide gives the aryl haloalkyl ether (4). Reduction of the aryl nitro group gives the substituted aniline (5) which undergoes reductive amination with Boc-(L)-homoserine lactol to give the protected diamine (6). An acylation/ring closure sequence is used to produce the protected aryl piperazinone (8), and the side chain alcohol is converted to the methyl sulfone (9) in a three step process.

Scheme 2 shows the conversion of this intermediate to the final radioiodinated compounds. Removal of the Boc protecting group and reductive amination gives the cyanobenzyl-imidazoylmethyl piperazinone (11). Conversion of the aryl bromide to the corresponding trimethylstannane (12) is followed by radioiodination which gives the final product (13).

Scheme 3 shows a general synthetic route that could be used to synthesize the fluorine-18 labelled farnesyl transferase inhibitors. The common intermediate for the labelling reaction would be the iodophenol (14) shown. The synthesis of this advanced intermediate would involve synthesizing the appropriate protected phenol following closely the chemistry depicted in Schemes 1 and 2. The protecting group shown in this scheme is the t-butyldiphenylsilyl group because it is compatible with the reaction conditions used in this synthetic scheme. Other protecting groups may be suitable. Commercially available 3,5-dinitrophenol (14) is reduced, diazotized and converted to 3-iodo-5-nitrophenol (16). The silyl protecting group is introduced and the nitro group is reduced to give the silyl protected 3-amino-5-iodophenol (18). The coupling of this intermediate (18) with commercially available Boc-L-methionine sulfone (19) (Bachem) and reduction of the resulting amide gives the diamine (20). This diamine (20) is converted to the piperazinone and coupled with 1-(4-cyanobenzyl)-5-formylimidazole (10), as described in U.S. Pat. No. 5,856,326 (herein incorporated by reference) in Example 42, to give the silyl protected phenylpiperizinone (22). The removal of the silyl protecting group gives the phenol that is the precursor for the fluorine-18 labelling chemistry. This phenol is then treated under basic conditions with the appropriate [$^{18}$F]bromofluoroalkane, or this phenol is converted to the appropriate alkyl aryl ether containing a leaving group which can be displaced with [$^{18}$F]fluoride ion.

The incorporation of a [$^{11}$C]-methyl moiety into a piperazinone containing FPTase inhibitor is shown in Scheme 4. Starting with a hydroxyethyl piperazinone (24), the hydroxy group is converted to the mesylate and then to the trityl protected thiol (25). A deprotection, condensation sequence is used to give the fully assembled compound (26).

The trityl group is removed using TFA/Et$_3$SiH, and the resulting thiol is methylated using [$^{11}$C]CH$_3$I and oxidized with OXONE to give the final C-11 labelled compound (27).

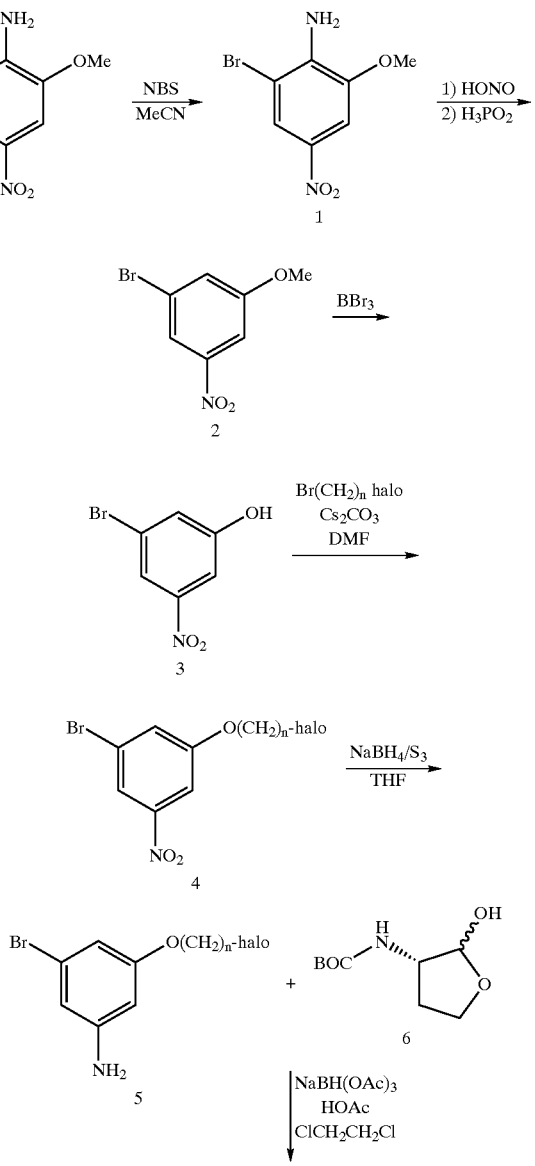

SCHEME 1

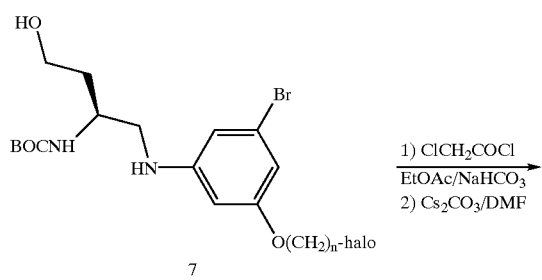
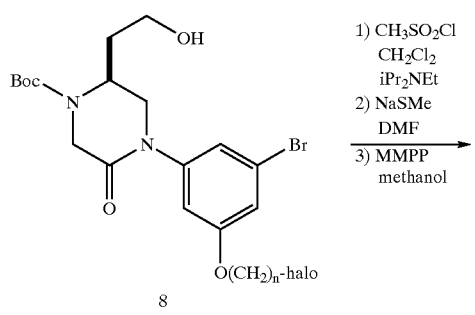
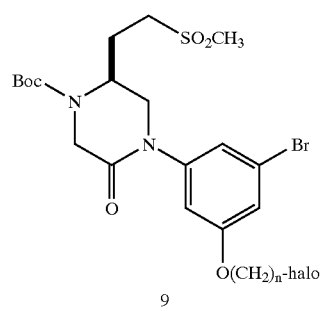
SCHEME 2
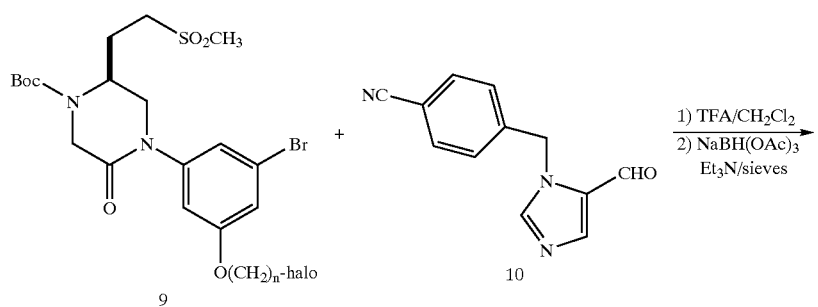
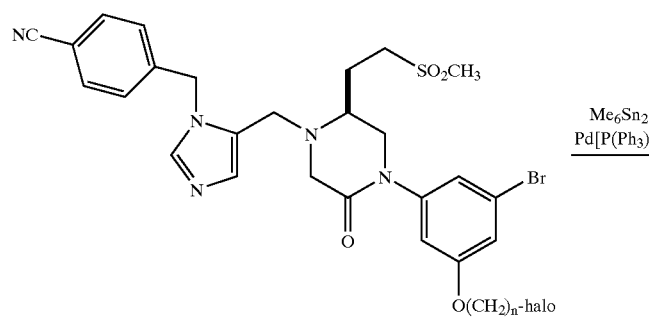

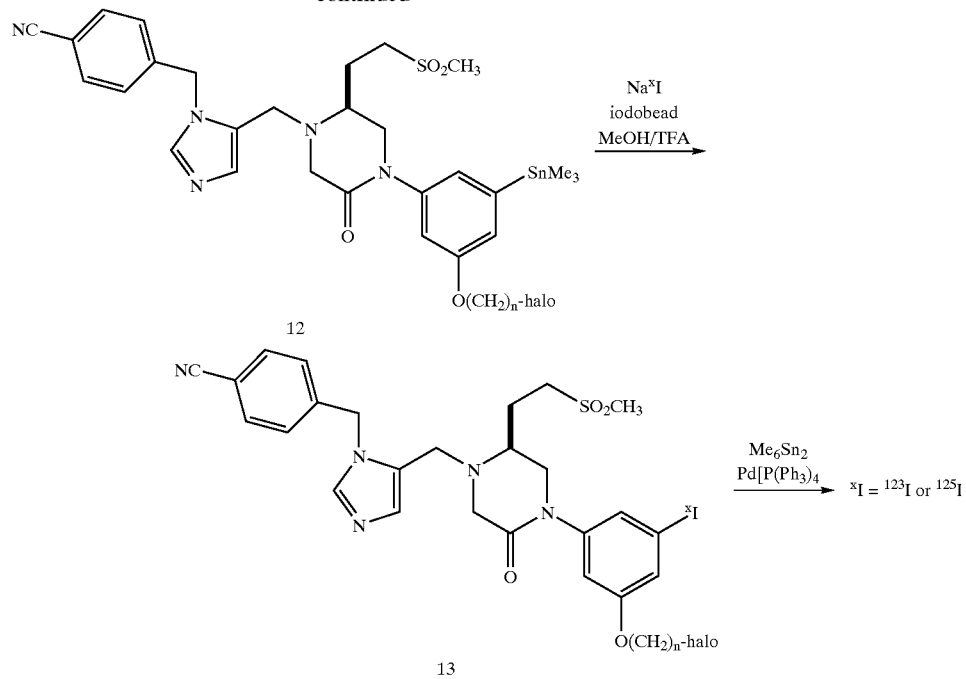

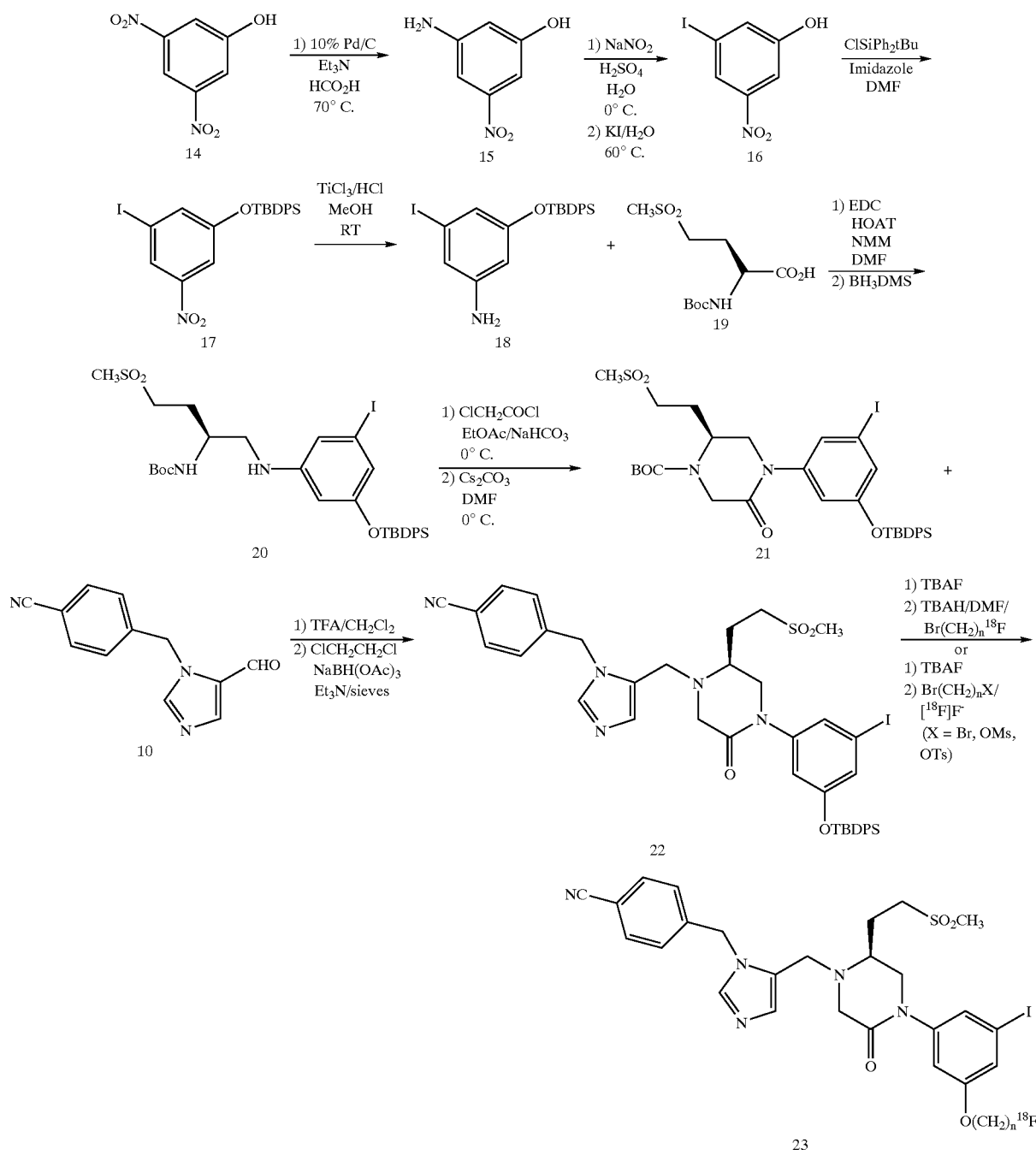

SCHEME 4

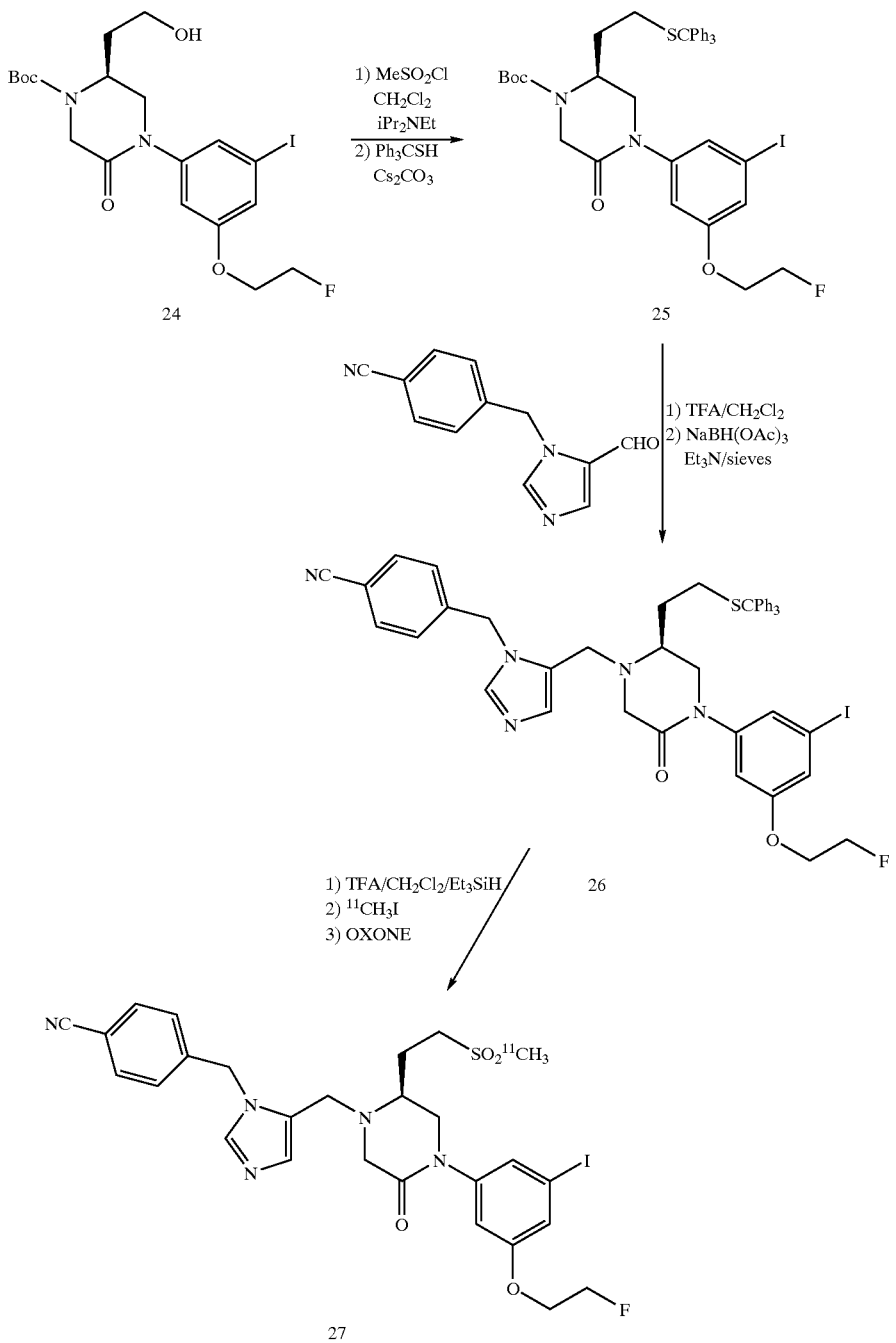

EXAMPLES

Examples provided are intended to assist in a further understanding of the invention. Particular materials employed, species and conditions are intended to be further illustrative of the invention and not limitative of the reasonable scope thereof.

Example 1

Preparation of (S)-1-(3-Fluoroethoxy-5-bromophenyl)-4-(t-butoxycarbonyl) -5-[(methanesulfonyl)ethyl -2-piperazinone Step A: 2-Bromo-6-methoxy-4-nitroaniline A clear yellow solution of 2-methoxy-4-nitroaniline (10 g, 15 59.5 mmol) in acetonitrile (300 mL) at room temperature was treated with N-bromosuccinimide (10.58 g, 59.5 mmol). The reaction was protected from light and stirred for 2 hours at room temperature. TLC (3:1 hexane:ethyl acetate) analysis showed starting material ($R_f$ 0.14) replaced with a higher spot ($R_f$ 0.23). The reaction was concentrated in vacuo, treated with carbon tetrachloride, filtered through celite and concentrated in vacuo to give 2-bromo-6-methoxy-4-nitroaniline as a yellow brown solid. $^1$H NMR (δ, CDCl$_3$): 8.11 (1H, d, J=2.2 Hz), 7.63 (1H, d, J=2.2 Hz), 4.96 (2H, br s), 3.96 (3H, s); MS (m/z) 249, 247.

Step B: 3-Bromo-5-nitroanisole

A mixture of 2-bromo-6-methoxy-4-nitroaniline, as described above in Step A, (450 mg, 1.82 mmol) in water (40 mL) was cooled to 0° C. and treated with sulfuric acid (1.1 mL) followed by a solution of sodium nitrite (125 mg, 1.82 mmol) in water (0.5 mL) via pipet over 5 minutes. After stirring for 45 minutes at 0° C., the reaction was treated with ice cold 50% $H_3PO_2$ (10 mL) and stirred for 1.5 hours at 0° C. The reaction was quenched by adding aqueous saturated $NaHCO_3$, filtered and dried overnight sitting in the hood to give an orange solid. This material was purified by column chromatography (5:1 hexane:ethyl acetate) to give 2-bromo-6-methoxy-4-nitroaniline and 3-bromo-5-nitroanisole as an off-white solid.

$^1$H NMR ($\delta$, MeOH-$d_4$): 7.96 (1H,m), 7.75 (1H,m), 7.53 (1H,m), 3.91 (3H,s); MS (m/z) 234, 232; mp 84–85° C.

Step C: 3-Bromo-5-nitrophenol

A solution of 3-bromo-5-nitroanisole, as described above in Step B, (2.4 g, 10.3 mmol) in methylene chloride (50 mL) was cooled to 0° C. and treated with boron tribromide (1M in $CH_2Cl_2$, 158 mL, 158 mmol), giving a clear purple solution. The reaction was warmed slowly to room temperature and stirred at room temperature overnight and heated at reflux for 2.5 hours. The reaction was poured into ice/water, the layers were separated and extracted with methylene chloride. The aqueous layer was neutralized with aqueous saturated $NaHCO_3$ and extracted with ethyl acetate. The organic layers were combined, dried ($MgSO_4$), filtered and concentrated in vacuo. This material was purified by column chromatography (10:1 to 5:1 hexane:ethyl acetate). The fractions containing the product contaminated with the bromoanisole were pooled, concentrated and purified using radial, thin layer chromatography (hexane to 5:1 hexane::ethyl acetate) to give 3-bromo-5-nitrophenol as a yellow solid.

$^1$H NMR ($\delta$, MeOH-$d_4$): 7.81 (1H, m), 7.57 (1H, m), 7.32 (1H, m).

Step D: 3-Bromo-5-fluoroethoxynitrobenzene

A solution of 3-bromo-5-nitrophenol, as described above in Step C, (1.04 g, 4.77 mmol) in dimethylformamide (30 mL) was cooled to 0° C. and treated with cesium carbonate (7.8 g, 23.8 mmol) giving an opaque red mixture. This mixture was treated with 1-bromo-2-fluoroethane (0.71 mL, 9.54 mmol) and the reaction was stirred overnight as the ice bath warmed to room temperature. The reaction was diluted with ethyl acetate/brine/aqueous saturated $NH_4Cl$, the layers were separated and the aqueous layer was extracted with ethyl acetate. The organic layers were combined, washed with brine, dried ($MgSO_4$), filtered and concentrated in vacuo to give an orange brown oil. This material was purified by radial, thin layer chromatography (hexane to 10:1 hexane: ethyl acetate) to give 3-bromo-5-fluoroethoxynitrobenzene as a clear yellow liquid.

$^1$H NMR ($\delta$, $CDCl_3$): 8.01 (1H, m), 7.71 (1H, m), 7.43 (1H, m), 4.88–4.69 (2H, m), 4.36–4.24 (2H, m); MS (m/z) 266, 264; mp 59–61° C.

Step E: 3-Bromo-5-fluoroethoxyaniline

A solution of 3-bromo-5-fluoroethoxynitrobenzene, as described above in Step D, (990 mg, 3.75 mmol) in tetrahydrofuran (22 mL) was added to a mixture of $NaBH_4/S_3$ (1.2 g) in tetrahydrofuran (15 mL) and the resulting mixture was placed in a 60° C. oil bath and heated overnight. The reaction was cooled to room temperature and concentrated using the rotary evaporator giving a yellow solid. Diethyl ether was added and 10% HCl until the pH was 1. The resulting mixture was filtered through celite and the layers were separated. The aqueous layer was washed with diethyl ether. The aqueous layer was made basic (pH>10) with diethyl ether present, the layers were separated and the aqueous layer was extracted with diethyl ether and ethyl acetate. The organic layers were combined and dried ($MgSO_4$), filtered and concentrated in vacuo to give 3-bromo-5-fluoroethoxyaniline as a yellow oil.

$^1$H NMR ($\delta$, $CDCl_3$): 6.47 (2H, m), 6.17 (1H, m), 4.81–4.62 (2H, m), 4.20–4.08 (2H, m); MS (m/z) 236, 234; mp 48.5–50° C.

Step F: (S)-1-N-(3-Fluoroethoxy-5-bromophenyl)-2-N-t-butoxycarbonyl-1,2-diamino-4-butanol A solution of 3-bromo-5-fluoroethoxyaniline, as described above in Step E, (600 mg, 2.56 mmol) and Boc-(L)-homoserine lactol, (573 mg, 2.82 mmol) in 1,2-dichloroethane (6 mL) at room temperature was treated with acetic acid (0.147 mL), stirred for 10 minutes, and then was treated with sodium triacetoxyborohydride (748 mg, 3.53 mmol). After stirring at room temperature for 2.5 hours, the reaction was poured into a separatory funnel containing methylene chloride and washed with aqueous saturated $NaHCO_3$. The organic layer was dried ($MgSO_4$), filtered and concentrated to give an orange foam. TLC analysis (2:1 hexane:ethyl acetate) shows unreacted aniline ($R_f$=0.17) and the desired product ($R_f$=0.05). The crude material was purified by radial, thin layer chromatography (3:1 to 1:2 hexane:ethyl acetate) to give the above-identified diamine.

$^1$H NMR ($\delta$, $CDCl_3$): 6.41 (2H, m), 6.13 (1H, m), 4.72 (2H, m), 4.74 (1H, d, J=8.5 Hz), 4.15 (2H, m), 4.01 (1H, m), 3.73 (2H, m), 3.16 (2H, m), 1.91 (1H, m), 1.49 (1H, m), 1.46 (9H, s); MS (m/z) 423, 421.

Step G: (S)-1-(3-Fluoroethoxy-5-bromophenyl)-4-(t-butoxycarbonyl)-5-hydroxyethyl-2-piperazinone A mixture of the diamine, as described above in Step F, (655 mg, 1.56 mmol) in ethyl acetate (10.5 mL) and aqueous saturated $NaHCO_3$ (10.5 mL) was cooled to 0° C. and treated with chloroacetyl chloride (0.137 mL, 1.72 mmol). After stirring for 2.5 hours at 0° C., the reaction was diluted with ethyl acetate/water. The layers were separated and the aqueous layer was extracted with ethyl acetate. The organic layers were combined, dried ($MgSO_4$), filtered and concentrated to give 670 mg of a white foam. This material was dissolved in dimethylformamide (14 mL), cooled to 0° C. and treated with cesium carbonate (3.33 g, 10.2 mmol). After stirring for 2.5 hours at 0° C., the reaction was diluted with ethyl acetate/brine/aqueous saturated $NH_4Cl$. The layers were separated and extracted with ethyl acetate. The organic layers were combined, washed with brine, dried ($MgSO_4$), filtered and concentrated to give a yellow oil. TLC analysis (1:1 hexane:ethyl acetate) shows the main spot with $R_f$=0.13. The crude material was purified by radial, thin layer chromatography (1:1 to 1:2 hexane:ethyl acetate) to give the hydroxyethyl piperazinone as an oil.

hu 1H NMR ($\delta$, $CDCl_3$): 7.05 (1H, m), 7.01 (1H, m), 6.83 (1H, m), 4.74 (2H, m), 4.61 (1H, m), 4.40 (1H, d, J=18.8Hz), 4.20 (2H, m), 4.13 (1H, m), 3.91 (1H, d, J=18.8 Hz), 3.73 (1H, m), 3.47 (2H, m), 1.85 (2H, m), 1.51 (9H, s); MS (m/z) 463, 461.

Step H: (S)-1-(3-Fluoroethoxy-5-bromophenyl)-4-(t-butoxycarbonyl)-5-[(methanesulfonyl)ethyl]-2-piperazinone A solution of (S)-1-(3-Fluoroethoxy-5-bromophenyl)-4-(t-butoxycarbonyl)-5-hydroxyethyl-2-piperazinone, as described above in Step G, (575 mg, 1.25 mmol) in methylene chloride (12 mL) was cooled to 0° C. and treated with N,N-diisopropylethylamine (0.432 mL, 2.5 mmol) and methanesulfonyl chloride (0.136 mL, 1.75 mmol). After stirring for 1.5 hours at 0° C. the reaction was poured into a separatory funnel containing 5% citric acid and the layers were separated. The aqueous layer was extracted with methylene chloride, dried (MgSO$_4$), filtered and concentrated to give 640 mg of a white foam. The mesylate was dissolved in dimethylformamide (17 mL), cooled to 0° C. and treated with sodium thiomethoxide (175 mg, 2.5 mmol). The reaction was stirred for three hours at 0° C. and then was poured into a separatory funnel containing ethyl acetate and washed with aqueous saturated NaHCO$_3$ and brine. The organic layer was dried (MgSO$_4$), filtered and concentrated to give 599 mg of a yellow oil. The $^1$H NMR (CDCl$_3$) shows the methyl singlet at 62.12. The methyl sulfide was dissolved in methanol (11 mL) at room temperature and treated with monoperoxyphthalic acid, magnesium salt (1.85 g, 3.74 mmol) in methanol (17 mL) and stirred at room temperature for 1.5 hours. The reaction was quenched with 2N Na$_2$S$_2$O$_3$, poured into a separatory funnel containing ethyl acetate/ aqueous saturated NaHCO$_3$ and the layers were separated. The organic layer was washed with brine, dried (MgSO$_4$), filtered and concentrated to give a yellow oil. TLC analysis (1:1 ethyl acetate:hexane) showed one main spot at R$_f$=0.09. This material was purified by radial, thin layer chromatography (1:1 to 1:2 hexane:ethyl acetate) to give the above-titled compound as a yellow foam.

$^1$H NMR (δ, CDCl3): 7.04 (2H, m), 6.84 (1H, m), 4.74 (2H, m), 4.57 (2H, m), 4.21 (2H, m), 4.09 (1H, m), 4.02 (1H, d, J=19.3 Hz), 3.49 (1H, dd, J=12.7, 1.95 Hz), 3.05 (2H, m), 2.96 (3H, s), 2.36 (1H, m), 2.16 (1H, m), 1.51 (9H, s); MS (m/z) 523, 525.

Example 2
Preparation of (S)-1-(3-Fluoroethoxy-5-bromophenyl)-4-[1-(4-cyanobenzyl) -5-imidazoylmethyl]-5-[(methanesulfonyl) ethyl]-2-piperazinone A solution of (S)-1-(3-Fluoroethoxy-5-bromophenyl)-4-(t-butoxycarbonyl)-5-[(methanesulfonyl)ethyl]-2-piperazinone, as described in Example 1, (512 mg, 0.98 mmol) in methylene chloride (12 mL) at room temperature was treated with trifluoroacetic acid (3.4 mL, 44.13 mmol) and stirred for 35 minutes at room temperature. The reaction was concentrated, treated with 1,2-dichloroethane (10.5 mL), triethylamine (10–15 drops until pH>7.5), 1-(4-cyanobenzyl)-5-formylimidazole, as described in U.S. Pat. No. 5,856,326, Example 42, Steps A–E, col. 79–80, (416 mg, 1.97 mmol), sodium triacetoxyborohydride (479 mg, 2.26 mmol) and molecular sieves. The reaction was stirred at room temperature and followed by HPLC [C18 μBondapak, 3.9×300 mm, 10% MeCN:H$_2$O(0.1% TFA) to 90% MeCN over 30 minutes with linear gradient, 1 mL/min, 220 and 254 nm] until the product was maximized (retention time=21 minutes). An additional portion of sodium triacetoxyborohydride was added. The reaction was stirred a total of two days. The reaction was diluted with methylene chloride, washed with aqueous saturated NaHCO$_3$ (emulsion forms), dried (MgSO$_4$), filtered and concentrated to give an orange oil. A portion of the crude material purified by radial, thin layer chromatography (2% methanol:chloroform to 5% methanol:chloroform) to give the desired product as an oil. $^1$H NMR (δ, CDCl$_3$): 7.67 (2H, d, J=8.3 Hz), 7.63 (1H, s), 7.14 (2H, d, J=8.3 Hz), 7.12 (1H, s), 7.01 (2H, m), 6.80 (1H, m), 5.33 (2H, s), 4.74 (2H, m), 4.20 (2H, m), 3.83 (1H, m), 3.64 (2H, m), 3.35 (2H, m), 3.2 (1H, m), 2.95 (1H, m), 2.91 (3H, s), 2.20 (2H, m); MS (m/z) 618, 620.

Example 3
Preparation of (S)-1-(3-Fluoroethoxy-5-trimethylstannyl)-4-[1-(4-cyanobenzyl)-5-imidazoylmethyl]-5-[(methanesulfonyl) ethyl]-2-piperazinone A solution of (S)-1-(3-Fluoroethoxy-5-bromophenyl)-4-[1-(4-cyanobenzyl)-5-imidazoylmethyl]-5-[(methanesulfonyl)ethyl]-2-piperazinone, as described in Example 2, (21.5 mg, 0.035 mmol) in 1,4-dioxane (0.87 mL) at room temperature was treated with hexamethylditin (25 μL) and tetrakis(triphenylphospine) palladium (0) (catalytic amount). The mixture was placed in a 100° C. oil bath and heated overnight. HPLC analysis (Waters C18 μBondapak, 3.9×300 mm, 40% MeCN:H$_2$O(0.1% TFA), 1 mL/min, 220 nm) shows unreacted starting material (8 minutes) along with the desired product (20 minutes). The reaction mixture was filtered through celite, rinsed with ethyl acetate and concentrated in vacuo to give a foam which was purified by radial, thin layer chromatography (5% methanol:chloroform) to give the desired product as an oil.

$^1$H NMR (δ, CDCl$_3$): 7.67 (2H, d, J=8.3 Hz), 7.61 (1H, m), 7.15 (2H, d, J=8.3Hz), 7.12 (1H, m), 6.99 (1H, m), 6.91 (1H, m), 6.74 (1H, m), 5.34 (2H, s), 4.74 (2H, m), 4.20 (2H, m), 3.83 (1H, m), 3.64 (2H, m), 3.35 (2H, m), 3.2 (1H, m), 2.95 (1H, m), 2.9 (3H, s), 2.20 (2H, m), 0.3 (9H, s); MS (m/z) 704.

Example 4
Preparation of [$^{125}$I](S)-1-(3-Fluoroethoxy-5-iodophenyl)-4-[1-(4-cyanobenzyl)-5-imidazoylmethyl]-5-[(methanesulfonyl)ethyl]-2-piperazinone To 5 mCi of NaI$^{25}$I (New England Nuclear #NEZ-033L) was added an iodobead, and after stirring for five minutes at room temperature, a solution of 0.1 mg of (S)-1-(3-Fluoroethoxy-5-trimethylstannyl) -4-[1-(4-cyanobenzyl)-5-imidazoylmethyl]-5-[(methanesulfonyl)ethyl]-2-piperazinone, as described in Example 3, in 50 μL of methanol containing 10 μL of trifluoroacetic acid, was added. After stirring for 3 minutes, 50 μL of a sodium metabisulfite solution (4.2 mg Na$_2$S$_2$O$_5$/mL H$_2$O) was added followed by 10 μL of ammonium hydroxide. This material was purified by HPLC (C18 Vydac protein and peptide column, 3.9×250 mm, 30% MeCN (0.1% TFA):H$_2$O(0.1% TFA), 1 mL/min) with the desired product eluting at 11.5 minutes. The fractions containing the center cut of the desired peak were concentrated and diluted with ethanol to give the above-titled compound.

Example 5
Preparation of [$^{123}$I](S)-1-(3-Fluoroethoxy-5-iodophenyl)-4-[1-(4-cyanobenzyl)-5-imidazoylmethyl]-5-[(methanesulfonyl)ethyl]-2-piperazinone To 17 mCi of Na$^{123}$I (Nordion # IPG-I-123) was added an iodobead, 50 μL of methanol and 20 μL of a Na$^{127}$I solution (13 μg/mL H$_2$O). This mixture was stirred for five minutes and then treated with 40 μL of a solution of (S)-1-(3-Fluoroethoxy-5-trimethylstannyl)-4-[1-(4-cyanobenzyl)-5-imidazoylmethyl]-5-[(methanesulfonyl)ethyl]-2-piperazinone, as described in Example 3, (10 mg/mL methanol) containing 10 μL of trifluoroacetic acid. After about 8 minutes at room temperature, the reaction was quenched with 10μL of sodium metabisulfite solution (10 mg Na$_2$S2O5/mL H$_2$O) and 15 μL of ammonium hydroxide. Purification by HPLC (C18 Vydac, protein and peptide column, 3.9×250 mm, 30% MeCN:H$_2$O(0.1% TFA), 1 mL/min, elution time=10.7 minutes) produced the above-titled compound.

Example 6
Preparation of (S)-1-(3-Fluoroethoxy-5-iodophenyl)-4-[1-(4-cyanobenzyl) -5-imidazoylmethyl]-5-([$^{11}$C] methanesulfonyl)ethyl]2-piperazinone
Step A: Preparation of [$^{11}$C]methyl iodide The preparation of [$^{11}$C]methyl iodide has been described in detail by Långströbm et al. (*J. Nucl. Med.*, 28:1037 (1987)). Two liters of ultra high purity nitrogen (Matheson Gas Products) are bombarded with protons accelerated by a small biomedical cyclotron (Scanditronix RNP-16). Carbon-11 in the form of carbon dioxide is formed by the reaction $^{14}$N(p,α)$^{11}$C. The target chamber is connected to the chemical processing by ⅛" stainless steel tubing.

The apparatus consists of the following: (1) a conical glass vessel (length=50 mm, i.d.=5 mm) connected to a reaction vessel equipped with a water-cooled reflux condenser (length=50 mm, i.d.=5 mm) via Teflon tubing (i.d. 1.5 mm) and electrovalves (General Valve Corp, Series 2) interfaced to a small computer (Hewlett Packard HP-85) for valve sequencing, (2) a heat gun (150° C.), (3) a 1 mL conical reaction vessel for trapping [$^{11}$C]methyl iodide, (4) a remote cooling (−78° C.) bath, (5) a high performance liquid chromatograph (sample equipment: Rheodyne Model 7126 injector, Waters Associates 6000A pump, Alltech Econosil $C_{18}$ 10 mm×25 cm column) equipped with a UV detector (Waters Associates Model 441) and a flow radio-activity detector, and (6) a rotary evaporator modified for remote addition and removal of solutions.

Ahead of this apparatus, there is a coil of stainless steel tubing (i.d.=2.2 mm) cooled by liquid nitrogen to retain $^{11}CO_2$ removed from the target under reduced pressure created by an oilless pump. Nitrogen is used as a sweep gas at a flow rate of 50 mL/min to sweep the radioactive gas through the above apparatus. This apparatus is evacuated and purged with argon prior to each synthesis to minimize carrier carbon contamination.

[$^{11}$C]$CO_2$ produced by 16 MeV proton irradiation of a nitrogen gas target is trapped in a cooled stainless steel coil at the end of bombardment. The cooling bath is removed and the trapped $CO_2$ is bubbled into the conical vessel containing 3.0 mg lithium aluminum hydride (Fluka Chemical Corp.) in 600 μL of tetra-hydrofuran. After the level of radioactivity in the vessel reaches a maximum, the vessel is heated by the heat gun to evaporate the tetrahydrofuran. Hydriodic acid (500 μL, 57% in water, Aldrich Chemical Co.) is then added to the hot vessel.

Step B: Preparation of (S)-1-(3-Fluoroethoxy-5-iodophenyl)-4-[1-(4-cyanobenzyl)-5-imidazoylmethyl]-5-([$^{11}$C]-methanesulfonyl) ethyl]2-piperazinone (S)-1-(3-Fluoroethxoy-5-iodophenyl)-4-(t-butoxycarbonyl)-5-hydroxyethyl-2-piperazinone (1 equiv.) (prepared as described for the bromo analog in Steps A–G in Example 1) is converted to its mesylate by using methanesulfonyl chloride (1.4 equiv.) in $CH_2Cl_2$ with iPr$_2$NEt (2 equiv.) The mesylate is then reacted with triphenylmethyl mercaptan (2 equiv.) in DMF with $Cs_2CO_3$ (5 equiv.) to give the trityl protected thiol product. As described in Example 2, removal of the Boc protecting group is accomplished by using excess TFA in $CH_2Cl_2$. After completion, reductive amination using 1-(4-cyanobenzyl)-5-formylimidazole (2 equiv.) in 1,2-dichloroethane with sodium triacetoxyborohydride (2.3 equiv) and molecular sieves and $Et_3N$ to adjust the pH to >7 is done to give (S)-1-(3-fluoroethxoy-5-iodophenyl)-4-[1-(4-cyanobenzyl)-5-imidazoylmethyl]-5-[(methanesulfonyl)ethyl]-2-piperazinone. Finally, the trityl protecting group is removed using excess TFA and $Et_3SiH$ (21 equiv) in $CH_2Cl_2$ to give the thioethylpiperazinone.

Step C: Preparation of (S)-1-(3-Fluoroethoxy-5-iodophenyl)-4-[1-(4-cyanobenzyl)-5-imidazoylmethyl]-5-([$^{11}$C]methanesulfonyl) ethyl]2-piperazinone A presaturated solution of $Cs_2CO_3$ in DMF is prepared by heating 3.75 mg of $Cs_2CO_3$ 500 μL of dry DMF at 80° C. for 10 min. A solution containing 1 mg of the thioethylpiperazinone, which is prepared as described above in Step B, in 200 μL of the presaturated solution of $Cs_2CO_3$ and an additional 1.36 mg of $Cs_2CO_3$ is added. This solution is cooled to −78° C. and [$^{11}$C]methyl iodide is added via transfer from the production apparatus by a stream of nitrogen carrier gas. When the level of radioactivity reaches a plateau, the stream of gas is stopped. The mixture is heated at 80° C. for 3 minutes then 200 μL of Oxone solution (20 mg in 200 μL of $H_2O$) is added and the solution stirred for 1 min. A 400 μL aliquot of HPLC eluent (40:60 MeCN:$H_2O$ (0.1% TFA) is added. The resulting solution is then filtered and the filtrate is injected onto the preparative HPLC. It is eluted with 40:60 (v:v) acetonitrile/water containing 0.1% trifluoroacetic acid. The radioactive peak corresponding to the desired product is collected in the rotary evaporator, and the solvent is evaporated under reduced pressure.

The residue is dissolved in sterile, normal saline (7 mL, sample label: Saline 0.9% injectable, U.S.P., Injection USP 0.9% sterile, nonpyrogenic; Abbott Laboratories, N. Chicago, Ill. 60064), filtered through a sterile, 0.22 μM filter (Sample label: Gelman Acrodisc, disposable filter assembly, sterile, nonpyrogenic) into a sterile, pyrogen free bottle (Sample label: 20 cc EVACUATED VIAL—sterile, pyrogen free; Medi-Physics/Amersham Company, Arlington Heights, Ill. 60005), and is diluted with sterile, sodium bicarbonate (3 mL, 8.4%) (Sample label: 8.4% Sodium Bicarbonate Inj., U.S.P.; Abbott Laboratories, N. Chicago, Ill. 60064).

Biological Assays

The ability of compounds of the present invention to inhibit cancer can be demonstrated using the following assays.

In vitro Inhibition of Farnesyl-Protein Transferase

Transferase Assays. Isoprenyl-protein transferase activity assays were carried out at 30° C. unless noted otherwise. A typical reaction contained (in a final volume of 50 μL): [$^3$H]farnesyl diphosphate or [3H] geranylgeranyl diphosphate, Ras protein, 50 mM HEPES, pH 7.5, 5 mM $MgCl_2$, 5 mM dithiothreitol and isoprenyl-protein transferase. The FPTase employed in the assay was prepared by recombinant expression as described in Omer, C. A., Kral, A. M., Diehl, R. E., Prendergast, G. C., Powers, S., Allen, C. M., Gibbs, J. B. and Kohl, N. E., (1993) *Biochemistry* 32:5167–5176. The geranylgeranyl-protein transferase-type I employed in the assay was prepared as described in U.S. Pat. No. 5,470,832, incorporated by reference. After thermally pre-equilibrating the assay mixture in the absence of enzyme, reactions were initiated by the addition of isoprenyl-protein transferase and stopped at timed intervals (typically 15 min) by the addition of 1 M HCl in ethanol (1 mL). The quenched reactions were allowed to stand for 15 m (to complete the precipitation process). After adding 2 mL of 100% ethanol, the reactions were vacuum-filtered through Whatman GF/C filters. Filters were washed four times with 2 mL aliquots of 100% ethanol, mixed with scintillation fluid (10 mL) and then counted in a Beckman LS3801scintillation counter.

For inhibition studies, assays were run as described above, except inhibitors were prepared as concentrated solutions in 100% dimethyl sulfoxide and then diluted 20-fold into the enzyme assay mixture. $IC_{50}$ values were determined with both transferase substrates near $K_M$ concentrations. Nonsaturating substrate conditions for inhibitor $IC_{50}$ determinations were as follows: FTase, 650 nM Ras-CVLS, 100 nM farnesyl diphosphate; GGPTase-I, 500 nM Ras-CAIL, 100 nM geranylgeranyl diphosphate.

In vivo Ras Prenylation Assay

The cell lines used in this assay consist of either Rat1 or NIH3T3 cells transformed by either viral Ha-ras; an N-ras chimeric gene in which the C-terminal hypervariable region of v-Ha-ras was substituted with the corresponding region from the N-ras gene; or ras-CVLL, a v-Ha-ras mutant in which the C-terminal exon encodes leucine instead of serine, making the encoded protein a substrate for geranylgeranylation by GGPTase I. The assay can also be performed using cell lines transformed with human Ha-ras, N-ras or Ki4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum, 400 $\mu$Ci[$^{35}$S]methionine (1000 Ci/mmol) and test compound(s). Cells treated with lovastatin, a compound that blocks Ras processing in cells by inhibiting the rate-limiting step in the isoprenoid biosynthetic pathway (Hancock, J. F. et al. *Cell,* 57:1167 (1989); DeClue, J. E. et al. *Cancer Res.,* 51:712 (1991); Sinensky, M. et al. *J. Biol. Chem.,* 265:19937 (1990)), serve as a positive control in this assay. After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the addition of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 $\mu$l of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/ SDS/0. 1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Partition Coefficient Protocol

Prior to assay, equal volumes of 1-octanol and pH 7.4 buffer are mutually saturated, allowed to settle, and separated into individual containers until use.

Standard solutions are prepared by dissolving an accurately weighed amount (1–2 mg) of the compound under study in a suitable solvent. Sample is dissolved in 10.00 ml spectral grade methanol although ethanol, acetonitrile or water may also be used provided the compound is completely soluble in that solvent. The solutions or appropriate dilutions are scanned by UV (HP 8452A Diode Array Spectrophotometer) to determine the wave length of maximum absorbance ($\lambda$max). The scan can also be obtained from the HPLC chromatogram of the methanol standard.

Partition sample solutions are prepared by placing an accurately weighed 1–2 mg of sample into a 20 ml scintillation vial and adding 10.00 ml of pH 7.4 buffer and 10.00 ml of 1-octanol which have been mutually saturated with each other. Vials are placed in the ultrasonic bath for 5 min. and then onto a flatbed shaker for at least 2 to 4 hrs. After agitation, vials are centrifuged at 1500 rpm for 10 min. and approximately 1 ml of each layer is removed to separate HPLC vials for analysis.

Measurement of concentration of the standard, octanol, and buffer solutions can be conducted either by absorbance in ultraviolet spectroscopy (Lw) or by peak areas in high performance liquid chromatography (HPLC) with the detector set at the compound's $\lambda$max. Currently, HPLC measurement is the method of choice. Appropriate dilutions, if necessary, should be made into the appropriate solvent.

Standard conditions of analysis are as follows:

Instrument—HP 1090 HPLC using either the diode array (DAD) or the variable wavelength detectors (VWD) set at the compound's $\lambda$max.

Column—Vydac Protein/Peptide C-18.

Solvent system—Gradient from 5–95% Acetonitrile/ H$_3$PO$_4$ Buffer over 10 min.; flow rate-3.0 ml/min.

Sample size—5 $\mu$l injection; larger injections (50, 100, 200 $\mu$l) can be used subsequently should no detectable peak result from the smaller injection.

Temperature—Ambient conditions.

$$\text{Partition Coefficient (PC)} = \frac{\text{(Octanol HPLC Area)(Octanol Dilution)}}{\text{(Buffer HPLC Area)(Buffer Dilution)}} \quad (a)$$

In vivo Enzyme Binding Studies

To determine the biodistribution of a radiotracer compound, 3–5 $\mu$Ci of radiotracer is injected (i.v. in 30% PEG/10% EtOH/H$_2$O) in male Sprague-Dawley rats (200–250 g). The animals are euthanized at 30 min., 120 min. and 360 min. after radiotracer injection. To determine the extent of specific binding to FPTase, an unlabeled FPTase inhibitor, such as (S)-1-(3-fluoroethoxy-5-bromophenyl)-4-[1-(4-cyanobenzyl)-5-imidazoylmethyl]-5-[(methanesulfonyl)ethyl]-2-piperazinone, as described in Example 2, (10 mpk or 5 mpk) is injected 30 min. prior to injection of the radiotracer, then the animals are euthanized at the times provided above. After euthanasia by cervical dislocation under light anesthesia, the thoracic aorta are cut and 1 ml of blood collected in heparinized syringes. Centrifugation for 2.5 minutes at 5000 rpm provides the plasma samples. The left ventricular muscle, left upper lobe of the lung, liver, kidney (cortex), both adrenals, spleen, pancreas, descending colon and prostate are removed, placed on ice and two 50 mg samples biopsied. For radiotracers with $^{125}$I labels, samples are counted, without further treatment, in an autogamma counter for 2 min. each. For tritium-containing radiotracers, tissues are dissolved by shaking in Biosolv (New England Nuclear) overnight. After neutralization of base with 0.5 N HCl, scintillation cocktail is added (in subdued light), samples dark adapted for several hours, then counted in a scintillation counter through several cycles to insure chemiluminescence is not significant. Data are expressed as %-injected dose/gm wet weight tissue.

To determine in vivo dissociation rates of radiotracer compound, 3–5 $\mu$Ci of radiotracer is injected (i.v. in 30% PEG/10% EtOH/H$_2$O) in male Sprague-Dawley rats (200–250 g). One hour after radiotracer injection, an unlabeled FPTase is injected i.v., and the animals are euthanized 60 min. after this "chase." For comparison, uninhibited binding is also determined at 60 and 120 min. post-injection of radiotracer (corresponds to 0 and 60 min. post-chase). Total enzyme signal is examined by preinjection of unlabeled FPTase inhibitor (5 mpk) 30 min. prior to radiotracer injection. After euthanasia, tissue samples are obtained and processed as described above.

Gamma Camera Imaging

Two rats are anesthetized (ketamine/ace-promazine), positioned on the camera head, and their tail veins cannulated for ease of injection. One rat is preinjected with an unlabeled FPTase inhibitor (10% EtOH/27% PEG/63% $H_2O$) 30 min. prior to injection of radiotracer to demonstrate non-specific binding. 150 $\mu$Ci/rat of an $^{123}$I labeled FPTase inhibitor is injected via its tail vein, and the catheters flushed with several mls of normal saline. Acquisition of images is started as the radiotracer is injected. Sixty, one minute images were acquired and the rats are subsequently euthanized with sodium pentobarbital. The images acquired during the first minute are dominated by blood flow, and as a result, provide good depiction of the heart, liver and kidneys. Regions of interest (ROIs) are drawn on the first image which includes a region defined as soft tissue (upper left chest), then used to analyze the count rates in subsequent images. The ROIs do not include the entire liver since radioactivity in adjacent tissues partially obscures these structures. Therefore, ROIs are defined to remain fairly clear during the course of the study, and are assumed to be representative of the entire organ. Radioactivity in the bladder was obtained from the final image. Count-rates are converted to %-dose/ROI by dividing the count-rate in the ROI by that of the whole rat, which is then multiplied by 100.

In vivo Occupancy Studies

Kinetics of enzyme occupancy by an unlabeled FPTase inhibitor (test compound) is determined by this assay. Thus, FVB mice are injected the test compound at either 40 mpk or 10 mpk subcutaneously (0.1 mls). Thirty minutes prior to euthanasia, 3 $\mu$Ci of tritiated farnesyl protein transferase inhibitor (radiotracer) was injected i.p. (0.2 mls 10%EtOH in 0.9% saline). Uninhibited binding of the radiotracer is determined by injection of the radiotracer in mice which have not received injection of the test compound. The mice are euthanized either 2 hours or 14 hours after injection of the test compound and lung, spleen, pancrease and blood are removed and processed as described above. Data are plotted as %-dose/g of tissue (wet weight).

PET Imaging in Dogs

Female beagle dogs weighing 7.7–14.6 kg (11.0±2.3 kg) are fasted for at least 12 hours allowing water intake ad libitum, and are premedicated with 0.3–0.4 mL Acepromazine injected i.m. on the day of the experiment. A 20 G two inch venous catheter is placed into the right front leg ulnar vein through which anesthesia is introduced by sodium pentobarbital 25–30 mg/kg in 3–4 ml and maintained with additional pentobarbital at an average dose of 3 mg/kg/hr. Another catheter is inserted into the contralateral ulnar vein for radiotracer administration.

Oxygen saturation of circulating blood is measured with a pulse oximeter (Nellcor Inc., Hayward, Calif.) placed on the tongue of the animal. Circulatory volume is maintained by intravenous infusion of isotonic saline. A 22 G cannula is inserted into the anterior tibial or distal femoral artery for continuous pressure monitoring (Spacelabs™, model 90603A). EKG, heart rate, and core temperature are monitored continuously. In particular, EKG is observed for ST segment changes and arrhythmias.

The animal is positioned in the PET camera and a tracer dose of [$^{15}$O]OH$_2$O administered via i.v. catheter. The image thus obtained is used to insure that the dog is positioned correctly to include liver, kidneys and pancreas. Subsequently, (S)-1-(3-fluoroethoxy-5-iodophenyl) -4-[1-(4-cyanobenzyl)-5-imidazoylmethyl]-5-[([$^{11}$C]methanesulfonyl)ethyl]-2-piperazinone, as described in Example 6, (<20 mCi) is administered via i.v. catheter. Following the acquisition of the total radiotracer image, an infusion is begun of the unlabeled FTI (test compound) at one of three dose rates (0.1, 1 or 10 mpk/day). After infusion for 2.5 hrs, (S)-1-(3-fluoroethoxy-5-iodophenyl)-4-[1-(4-cyanobenzyl)-5-imidazoylmethyl]-5-[([$^{11}$C]methanesulfonyl)ethyl]-2-piperazinone is again injected via the catheter. Images are again acquired for up to 90 min. Within ten minutes of the injection of radiotracer and at the end of the imaging session, 1 ml blood samples are obtained for determining the plasma concentration of test compound. In one imaging session, a dose of 10 mpk (S)-1-(3-fluoroethoxy-5-bromophenyl)-4-[1-(4-cyanobenzyl)-5-imidazoylmethyl]-5-[(methanesulfonyl)ethyl]-2-piperazinone, as described in Example 2, is infused over 5 minutes. This dose has been determined to completely block radiotracer binding and thus is used to determine the maximum enzyme-specific signal obtained with the PET radiotracer. At the conclusion of the study, animals are recovered and returned to animal housing.

For uninhibited distribution of radiotracer, regions of interest (ROIs) are drawn on the reconstructed image includes the kidney cortex and a region of liver which is removed from the gallbladder images. These regions are used to generate time activity curves obtained in the absence of test compound or in the presence of test compound at the various infusion doses examined. Data are expressed as radioactivity per unit time per unit volume ($\mu$Ci/cc/mCi injected dose). Inhibition curves are generated from the data obtained in a region of interest obtained starting at 70 min. post-injection of radiotracer. At this time, clearance of non-specific binding has reached steady state. The ID$_{50}$ values were obtained by curve fitting the dose-rate/inhibition curves with equation iii, hereinabove.

Cell Radiotracer Assay of Farnesyl Transferase Inhibitors (CRAFTI)

This assay measures the competition between a farnesyl transferase inhibitor (FTI) and a radiolabeled FTI for binding to high affinity sites (presumably farnesyl transferase) in living cells.

Fresh radiotracer [$^{125}$I](S)-1-(3-fluoroethoxy-5-iodophenyl) -4-[1-(4-cyanobenzyl)-5-imidazoylmethyl]-5-[(methanesulfonyl)ethyl]-2-piperazinone, as described in Example 4, is synthesized monthly, with a specific activity of ~350–1400 Ci/mmole. CRAFTI is run routinely using a Rat1 fibroblast line transformed by v-Ha-ras (Hras/rat1). CRAFTI is performed by growing cells under anchorage-dependent conditions in 24-well tissue culture plates overnight, to achieve near confluent monolayers of cells. Radiotracer is diluted in cell growth media to a concentration of ~1 nM (~1 $\mu$Ci/ml), and vehicle or test FTI (in log dilutions, 6 point titration) is added to the diluted tracer. The growth media is removed from the cell monolayers, and 0.65 ml of the diluted radiotracer/test FTI mixture is applied. After 4 hr incubation, the tracer is removed by aspiration, the monolayers are rinsed quickly with 2 ml PBS, and the cells are trypsinized and transferred to tubes for gamma counting. Dose-inhibition curves and IC$_{50}$s are determined by curve-fitting the equation:

$$\text{Radiotracer Bound} = \frac{A_o - (A_o \times [I_o])}{([I_o] + IC_{50}) + NS}$$

where $A_0$ is the count-rate of radiotracer in the absence of inhibitor, $I_0$ is the concentration of added FTI, $IC_{50}$ is the concentration of FTI that inhibits 50% of radiotracer binding and NS is the extent of non-specific binding.

What is claimed is:

1. A radiolabeled farnesyl-protein transferase inhibitor compound of the formula I

I wherein

R is $O(CH_2)_n$halo;

X is $^3H$, $^{11}C$, $^{18}F$, $^{125}I$, $^{82}Br$, $^{123}I$, $^{124}I$, $^{131}I$, $^{75}Br$, $^{76}Br$, $^{15}O$, $^{13}N$, $^{211}At$, or $^{77}Br$; and n is 1 to 6;

or a pharmaceutically acceptable salt thereof.

2. The radiolabeled compound according to claim 1 wherein X is $^{125}I$, $^{123}I$, $^{124}I$, $^{82}Br$, $^{75}Br$, $^{76}Br$, or $^{77}Br$.

3. The radiolabeled compound according to claim 1 wherein X is $^{125}I$ or $^{123}I$.

4. A radiolabeled farnesyl-protein transferase inhibitor compound of the formula I

I wherein

R is $O(CH_2)_n{}^{18}F$;

X is $^{127}I$; and n is 1 to 6;

or a pharmaceutically acceptable salt thereof.

5. A radiolabeled farnesyl-protein transferase inhibitor compound of the formula II

II wherein

R is $O(CH_2)_n$halo

X is $^{127}I$; and n is 1 to 6;

or a pharmaceutically acceptable salt thereof.

6. A radiolabeled compound which is or a pharmaceutically acceptable salt thereof.

7. A pharmaceutical composition comprising a pharmaceutical carrier, and dispersed therein, a therapeutically effective amount of a compound of claim 1.

* * * * *